(12) United States Patent
Nozawa et al.

(10) Patent No.: US 7,443,502 B2
(45) Date of Patent: Oct. 28, 2008

(54) ABSORPTION SPECTRUM PHOTOMETRY MICROCHIP TESTING DEVICE AND COMPONENTS THEREOF

(75) Inventors: Shigenori Nozawa, Himeji (JP); Shigeki Matsumoto, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/281,481

(22) Filed: Nov. 18, 2005

(65) Prior Publication Data

US 2006/0103848 A1    May 18, 2006

(30) Foreign Application Priority Data

Nov. 18, 2004    (JP)    ............................. 2004-333925

(51) Int. Cl.
*G01N 21/01*    (2006.01)
(52) U.S. Cl. ...................................... 356/244; 356/432
(58) Field of Classification Search ................. 356/244, 356/246, 432–443
See application file for complete search history.

(56) References Cited

U.S. PATENT DOCUMENTS

| | | | | |
|---|---|---|---|---|
| 4,066,362 A | * | 1/1978 | Carter | ......................... 356/409 |
| 5,221,961 A | * | 6/1993 | Shen | ........................... 356/432 |
| 5,638,171 A | * | 6/1997 | Honig et al. | ................. 356/244 |
| 6,839,140 B1 | * | 1/2005 | O'Keefe et al. | ............. 356/436 |
| 2002/0180963 A1 | * | 12/2002 | Chien et al. | .................. 356/246 |
| 2003/0036206 A1 | * | 2/2003 | Chien et al. | .................. 436/180 |

FOREIGN PATENT DOCUMENTS

| | | |
|---|---|---|
| CA | 2 479 695 A1 | 9/2003 |
| EP | 0 201 824 A2 | 11/1986 |
| EP | 1 489 403 A1 | 12/2004 |
| JP | 2003-344266 A | 12/2003 |
| JP | 2003-344267 A | 12/2003 |
| JP | 2004077305 A * | 3/2004 |

* cited by examiner

*Primary Examiner*—Tarifur R Chowdhury
*Assistant Examiner*—Jonathon D Cook
(74) *Attorney, Agent, or Firm*—David S. Safran

(57) ABSTRACT

A microchip testing device with a microchip having an absorbance measuring chamber for measuring absorbance, a transmitted light receiving unit for receiving light which has been emitted from a light source and has been transmitted through the absorbance measuring chamber, an aperture which extends in a straight line in the direction of the optical axis of the absorbance measuring chamber, with an entry opening for the light emitted by the light source on one end and a light exit opening on an opposite end from which the light enters the absorbance measuring chamber, an incident light beam splitter which is located in the optical path between the light exit opening of the aperture and the absorbance measuring chamber and which transmits part of the incident light and reflects another part of it, and a reflected light receiving part for receiving the light which has been reflected by the beam splitter.

4 Claims, 4 Drawing Sheets

ABSORPTION SPECTRUM PHOTOMETRY MICROCHIP TESTING DEVICE AND COMPONENTS THEREOF

BACKGROUND OF THE INVENTION

1. Field of the Invention

The invention relates to a microchip testing device for measuring the concentration of a component which is to be determined in a test liquid by means of absorption spectrum photometry using a microchip. Furthermore, the invention also relates to a microchip and microchip holder comprising this microchip testing device.

2. Description of Related Art

Recently an analysis process using a microchip called "μ-TAS" (μ-Total Analysis System) or "Lab-on-a-chip" has been attracting attention in which, using micromachinery production technology, chemical analyses and the like are performed in a more detailed manner than with conventional devices.

In this analysis system using a microchip (hereinafter also called a "microchip analysis system"), the effort is made to carry out all analysis treatment steps, such as mixing of the reagents, reactions, precipitations, extractions, determinations and the like, in an extremely small channel which is formed on a small substrate by micromachinery production techniques. Specifically, it is used, for example, for analyses of blood in the field of medicine, analyses of protein in extremely small amounts, analyses of molecules of living organisms, such as nucleic acids, and the like.

In particular, in the case of using a microchip analysis system for analyses of human blood, there are the following advantages:

1. For example, since only a small amount of blood is sufficient, the burden on the patient can be reduced.
2. Since only a small amount of reagent is sufficient, the analysis costs can be reduced.
3. Since the device is small, analyses can be easily carried out.

It is being checked, whether using these advantages for a blood analysis device by the microchip analysis system, a specification can be stipulated in which the patient himself can analyze his blood, for example, at home or the like.

In a microchip analysis system, generally absorption spectrum photometry is used to measure the concentration of the portion of the substance which is to be determined in a test liquid (hereinafter, also called the "liquid to be tested"). Specifically, a microchip testing device is proposed in which the following actions were performed (see, for example, JP-A-2003-279471):

A mixture which contains an absorbance component which was obtained by adding a reagent to the liquid to be tested is allowed to flow into a channel which is formed, for example, in a microchip; the linear region of this channel is defined as the chamber for measuring absorbance;

the light, which was emitted by the light source and was transmitted by the chamber for measuring absorbance, is received by a light receiving part and the absorbance is determined; and based on this absorbance, the concentration of the portion of the substance to be determined in the liquid to be tested was computed.

In this microchip testing device, the amount of the liquid to be tested and the amount of reagent are extremely small. Furthermore, the absorbance measuring chamber must have at least a certain length according to the type of liquid to be tested. Therefore, for the chamber for measuring absorbance, it is necessary to have an extremely narrow shape and to make the surfaces of the light incidence part and light exit part very small (for example, roughly 0.5 mm$^2$). For exact measurement of the absorbance, it is therefore necessary to prevent the light from emerging to the outside from the side of the absorbance measuring chamber by allowing light with high parallelism to be incident in the chamber for measuring absorbance, and thus, to prevent measurement errors from arising due to faulty radiation.

Here, the expression "faulty radiation" is defined as light which passes through a region outside the absorbance measuring chamber in the microchip and which is incident in the light receiving part.

The use of a laser device as the light source is ideal for supply of light to the chamber for measuring absorbance. However, since the laser light is monochromatic light and since, moreover, depending on the type of portion of the substance which is to be determined, the wavelength of the light which is necessary for measurement is different, it is necessary to provide a suitable laser device for each measurement; this is laborious and causes high testing costs. Therefore, use of a discharge lamp, such as a xenon lamp or the like, which emits light in a continuous wavelength range in combination with a wavelength selection means, such as a wavelength selection filter or the like, is being tested.

However, in a microchip testing device, the following is determined:

The intensity of the light (hereinafter called the "transmitted light intensity") which emerges after passage through the absorbance measuring chamber into which the mixture has been introduced;

Based on this transmitted light intensity and the intensity of the light which is incident in the absorbance measuring chamber (hereinafter also called the "incident light intensity") which was measured beforehand by, for example, pure water being introduced into the absorbance measuring chamber and measuring the intensity of the light which is transmitted and emerges from the absorbance measuring chamber into which this pure water was introduced, the concentration of the portion of the substance to be determined is computed according to the Lambert-Beer Law.

In the case of using a discharge lamp, such as xenon lamp or the like, as the light source, there is the disadvantage that there is the danger that the value of the incident light intensity measured beforehand will differ greatly from the actual incident light intensity at the instant of measurement of the transmitted light intensity, since the discharge lamp has the property of changing the amount of radiant light over time, so that sufficient measurement accuracy cannot be obtained. This disadvantage is serious if there is a great time difference between the instant of measurement of the incident light intensity and the instant of measuring the transmitted light intensity.

SUMMARY OF THE INVENTION

The invention was devised to eliminate the above described disadvantage in the prior art. Thus, a primary object of the present invention is to devise a microchip testing device in which high measurement accuracy is obtained even in the case of using a discharge lamp as the light source.

Another object is to devise a microchip and chip holder which can be used for a microchip testing device.

These objects are achieved in a microchip testing device in accordance with the invention which comprises:

a microchip with an absorbance measuring chamber and a transmitted light receiving unit for receiving light which has been emitted from a light source and which has been transmitted by the chamber for measuring absorbance, in which:

an aperture extends in a straight line in the direction of the optical axis of the chamber for measuring absorbance, with an entry opening for the light emitted by the light source on one end and a light exit opening on the other end through which the light enters the chamber for measuring absorbance;

a beam splitter of incident light is located in the optical path between the light exit opening of the aperture and the absorbance measuring chamber and is made such that it transmits one part of the incident light and reflects another part of it; and a reflected light receiving part for receiving the light reflected by the beam splitter.

These objects are furthermore advantageously achieved in a microchip testing device in accordance with the invention in that it has a chip holder with a space for inserting the microchip into which a microchip is inserted.

These objects are also advantageously achieved in a microchip testing device according to the invention in that the microchip has a projection with a surface which is opposite the end from which the light emerges from the aperture, this projection surrounding the chamber for measuring absorbance.

Still further, these objects are achieved in a microchip in accordance with the invention which is a component of the microchip testing device in that there is a beam splitter of incident light.

These objects are, moreover, achieved in a chip holder according to the invention which is a component of the microchip testing device in that there are an aperture and a beam splitter of incident light.

Action of the Invention

The microchip testing device of the invention yields the following effects:

1. In the chamber for measuring absorbance, the aperture forms a light guidance path for selective introduction of light which travels from the light source in a straight line to the chamber for measuring absorbance. In this way, light with high parallelism can be allowed to be incident in this chamber for measuring absorbance.
2. A means for measuring the incident light intensity is formed from the beam splitter of incident light which is located in the optical path which travels from one end of the aperture to the absorbance measuring chamber and from the reflected light receiving part. Therefore, the incident light intensity can be measured based on the light which is incident in the aperture together with the measurement of the transmitted light intensity.
3. Therefore, even for a change of the amount of radiation of the light emitted by the light source which occurs over time, as a result only one of the measured values of the incident light intensity and of the transmitted light intensity which are used for computing the concentration of the portion of the substance which is to be determined is prevented from fluctuating.
4. Moreover, an exact value of the incident light intensity of the light which is introduced into the absorbance measuring chamber can be obtained.
5. Therefore, the concentration of the portion of the substance to be determined in the test liquid can be measured with high accuracy.

The microchip in accordance with the invention and the chip holder of the invention are used as material components of the above described microchip testing device.

The invention is further described below using several embodiments shown in the drawings.

DETAILED DESCRIPTION OF THE INVENTION

FIRST EMBODIMENT

Figure 1:
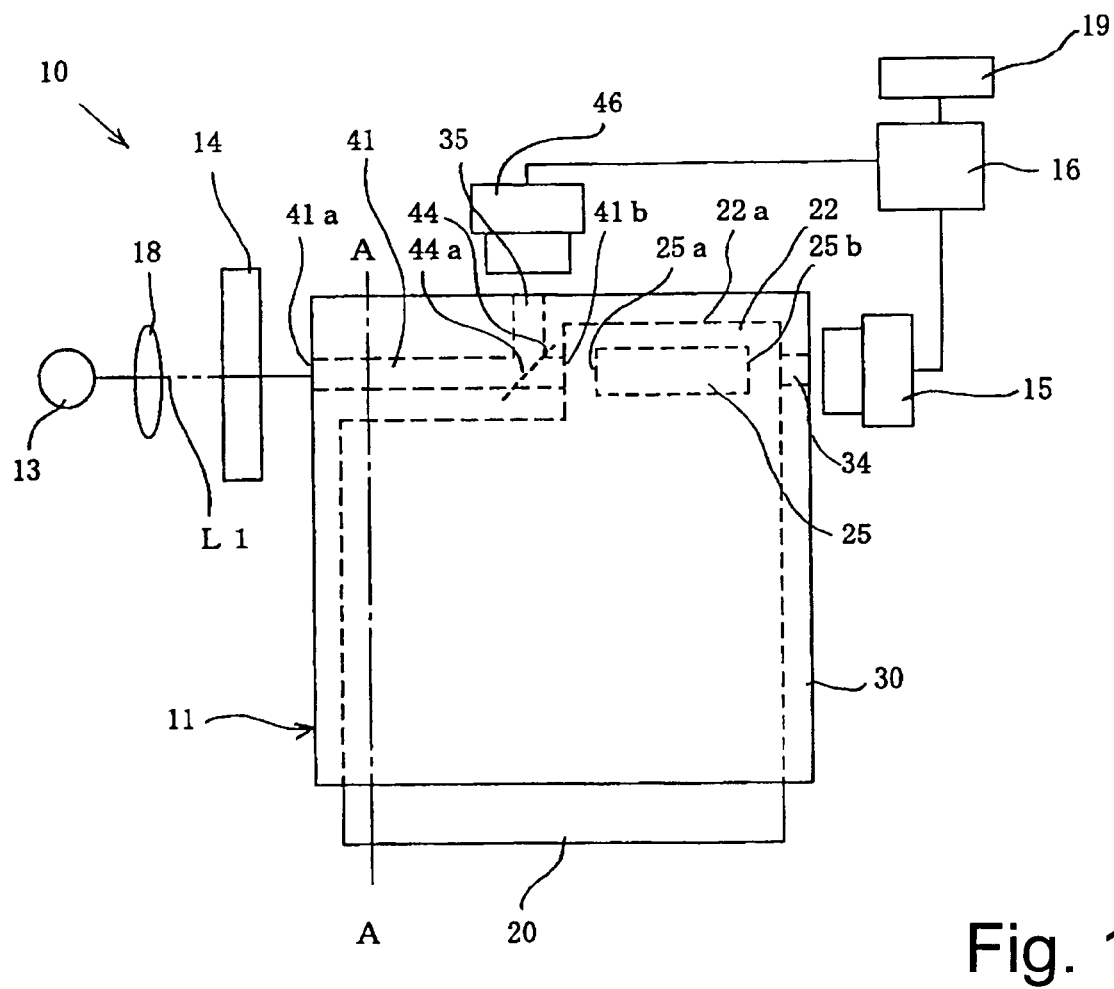
FIG. 1 is a schematic of one example of the arrangement of a microchip testing device in accordance with the invention.
Figure 2:
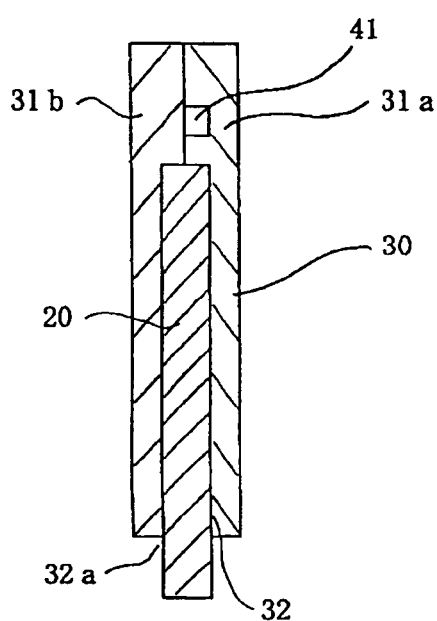
FIG. 2 is a sectional view of the microchip testing device taken alone line A-A in FIG. 1.

FIG. 1 shows a schematic of one example of the arrangement of the microchip testing device 10 in accordance with the invention which has an absorbance measuring chamber 25 and a chip holder 30 with a space 32 for receiving the microchip 20, which is shown inserted in the figure. The device 10 is used to measure the concentration of the portion of the substance to be determined in a liquid to be tested (test liquid) by absorption spectrum photometry.

The first embodiment of the microchip testing device 10 is a plate-like body which has a projection 22 in one of its end regions (in the top region in FIG. 1) and is made of a transparent material, such as, for example, a plastic, like polyethylene terephthalate (PET) or the like. The device 10 comprises:

a main body 11, for example, an aluminum box, in which the microchip 20 is inserted, through an opening 32a, into the space 32 of the chip holder 30. In the microchip 20, within the projection 22, a chamber 25 for measuring absorbance is formed from a space in the form of a rectangular parallelepiped which extends across the projection 22 parallel to its surface (to the left and right in FIG. 1);

a light source 13 for supplying light to the chamber 25 for measuring absorbance;

a wavelength selection filter 14 which is located in the optical path L1 in which the light emitted from the light source 13 reaches the main body 11 of the device and which is shown in FIG. 1 using a double broken line;

a transmitted light receiving unit 15 which is located on the opposite side of the main body 11 of the device the wavelength selection filter 14 and the light source 13 and which receives the light which has been transmitted through the chamber 25 for measuring absorbance; and an operation part 16 which is connected to the transmitted light receiving unit 15 and is used to compute the concentration of the portion of the substance to be determined based on the measured absorbance.

In the embodiment in this representation, for the main body 11 of the device, the microchip 20 is positioned so that the end face 22a of the projection 22 abuts the inside wall which is opposite the opening 32a of the chip holder 30. In this way, the microchip 20 is installed at a given location. Furthermore, a smoothing lens 18 and a display part 19 in which the value computed in the operation part 16 is displayed are provided.

Figure 3:
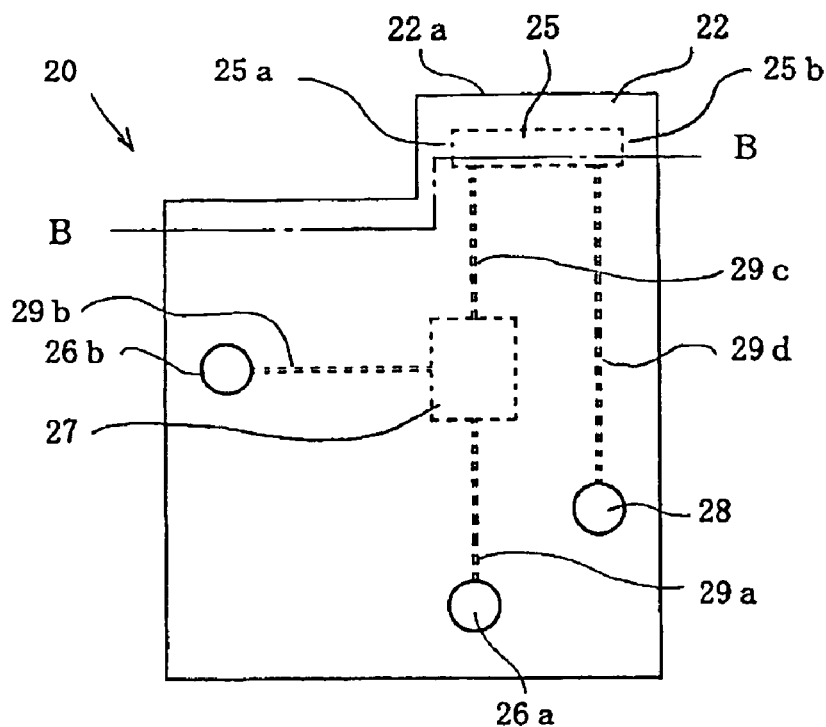
FIG. 3 is a schematic representation of a microchip which is contained in the microchip testing device as shown in FIG. 1.
Figure 4:
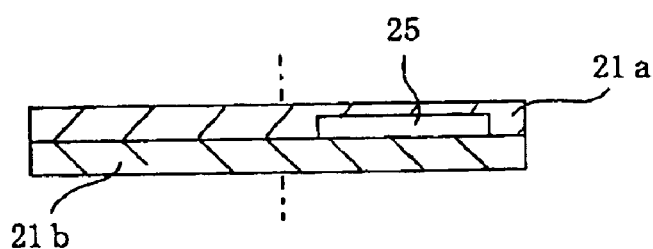
FIG. 4 is a cross-sectional view of the microchip taken along line B-B in FIG. 3.

The microchip 20, as shown in FIGS. 3 & 4, is produced by cementing two substrates 21a, 21b together. The substrate 21a is provided with a concave site for measuring the absorbance which is hermetically sealed by the other substrate 21b which is superimposed on the substrate 21a. In this way the absorbance measuring chamber 25 is formed.

In this embodiment, as shown in FIG. 3, the microchip 20 comprises the following:
the absorbance measuring chamber 25;
an opening 26a for injection of the liquid to be tested, which has an inlet at the outer surface of the substrate 21a;
an opening 26b for injection of reagent;
an outlet opening 28;
a mixing chamber 27 formed by a recess in the substrate 21a that is hermetically sealed by the substrate 21b;
a channel 29a for the liquid which is to be tested, which continuously connects the opening 26a to the mixing chamber 27;
a channel 29b for reagent, which continuously connects the opening 26b to the mixing chamber 27;
a channel 29c for mixing which continuously connects the mixing chamber 27 to the absorbance measuring chamber 25; and
an outlet channel 29d which continuously connects the absorbance measuring chamber 25 to the outlet opening 28.

The chamber 25 for measuring absorbance is supplied with a mixture which contains an absorbance component which was obtained by mixing the liquid which is to be tested and which was supplied to the opening 26a with the reagent which was supplied to the opening 26b in the mixing chamber 27. This mixture accordingly passes through the chamber 25 and is finally released from the outlet opening 28.

In the first microchip testing device 10, in the chip holder 30 comprising the main body 11 of the device, there are an aperture 41 and a half mirror 44. The aperture 41 extends in the direction of the optical axis (to the left and right in FIG. 1) of the absorbance measuring chamber 25 in a straight line and delivers the light which has been emitted by the light source 13 and which is incident from one end 41a of the chamber (the left end in FIG. 1) through the exit opening on the other end 41b (the right end in FIG. 1) into the chamber 25 for measuring absorbance. The half mirror 44 is arranged such that it crosses the aperture 41 and reflects part of the incident light, transmits the remainder and thus divides the incident light into two light portions. Outside of the main body 11 of the device (top in FIG. 1) is the reflected light receiving part 46 for receiving the light reflected by the half mirror 44. It is connected to the operating part 16.

In the example in this representation, the half mirror 44 is in a state in which its light incidence surface 44a is inclined at an angle of 45° relative to the optical axis of the aperture 41. The light guidance path 35 directs the light reflected by the half mirror 44 into the reflected light receiving part 46. It is continuously connected to the aperture 41. Furthermore, a transmitted light guidance path 34 directs the light which has been transmitted through the chamber 25 and has emerged from the light exit surface 25b into the transmitted light receiving unit 15.

For the aperture 41, it is advantageous that it is a tunnel-like light guidance path with a square cross sectional shape with an opening diameter that is smaller than the minimum diameter of the light incidence surface 25a of the chamber 25 for measuring absorbance. Furthermore, it is advantageous that the ratio (a/b) of the opening diameter (a) of the aperture to the total length (b) of the aperture is 0.01 to 0.02.

As a specific example of the dimensions of the aperture 41 in conjunction with the light incidence surface 25a of the absorbance measuring chamber 25, at a minimum diameter of 0.7 mm of the light incidence surface 25a of the absorbance measuring chamber 25, the opening diameter is 0.3 mm, the total length is 16 mm, and moreover, the ratio (a/b) of the opening diameter to the total length is 0.019 at the aperture 41.

Furthermore, for the aperture 41 it is advantageous that its inner side has an antireflection coating or is otherwise process to minimize reflection. The antireflection processing is suitably selected depending on the material and the like of the chip holder 30. In the case, for example, in which the chip holder 30 is made of aluminum, black anodization of the aluminum, or the like, is suitable.

A layered structure or the like in which, for example, a dielectric, multilayer film is provided on a glass plate can be used as the half mirror 44.

A chip holder 30 can be produced from the following components as follows:

Components:
a substrate 31a in which a recess for inserting the microchip, a recess for the aperture, a recess for the light guidance path for the reflected light, a recess for the light guidance path for transmitted light and a recess for installation of a half-mirror are formed,
a substrate 31b in which only a recess for completing the space for inserting the microchip is formed; and
a half mirror.

Production Steps:
The half mirror 44 is installed at the recess for the installation of the half mirror of the substrate 31a.
Afterwards the substrate 31a in which the half mirror 44 is installed is cemented to the substrate 31b in such as way that a space 32 for inserting the microchip is formed by a combination of recesses in the substrates 31a, 31b.

A xenon lamp or an ultrahigh pressure mercury lamp and a metal halide lamp of the short arc type and the like, which are advantageously used as the light source of a projector, can be used as the light source 13. However, it is advantageous to use a xenon lamp of the short arc type with a power consumption from 20 W to 75 W. The reason for this is the following:

High irradiance can be obtained.
It is easy to obtain a point light source.
The lamp has a continuous spectrum in a wide wavelength range from 250 nm to 1400 nm.
Especially in the wavelength range which is often used for measuring the absorbance (specifically in the wavelength range from 300 nm to 800 nm), intensive lines do not form, and stable radiation spectra can be obtained.

The wavelength selection filter 14 has a high light transmission factor only with respect to light in the wavelength range which is absorbed by the absorbance component in the mixture which is delivered into the absorbance measuring chamber 25 (hereinafter also called "light in the measurement wavelength range"). For example, a wavelength selection filter can be used in which a dielectric, multilayer film or a metallic film is provided on a glass plate.

The transmitted light receiving unit 15 and the reflected light receiving part 46 each have the function of outputting light intensity signals according to the received light. Specifically, light receiving elements, such as, for example, a silicon photodiode or the like, can be used as the transmitted light receiving unit 15 and the reflected light receiving part 46. The silicon photodiode is a light receiving element which has sensitivity to light in the wavelength range from 300 nm to 1100 nm.

The operation part 16 is connected to the transmitted light receiving unit 15 and the reflected light receiving part 46 and has an arithmetic-logic unit which computes the concentration of the portion of the substance to be determined in the liquid to be tested according to the Lambert-Beer Law based on the light intensity signal which was output from the transmitted light receiving unit 15 (hereinafter also called "transmitted light signal") and based on the light intensity signal which was output from the reflected light receiving part 46 (hereinafter also called the "reflected light signal").

The first microchip testing device 10 with this arrangement is shifted into the operating state as follows:

A liquid to be tested is supplied to the opening 26a for injection of the liquid of the microchip 20 to be tested.
Reagent is supplied to the opening 26b for injection of reagent.
A mixture is obtained in the mixing chamber 27, for example, by the action of a suction pump which is connected to the outlet opening 28 and is delivered into the absorbance measuring chamber 25.
Afterwards, the microchip 20 is installed in the chip holder 30 and the light source 13 is turned on.

In the first microchip testing device 10, in the operating state, the light in the measurement wavelength range which was emitted by the light source 13, made parallel by the smoothing lens 18 and transmitted by the wavelength selection filter 14, is divided into two light portions after incidence in the aperture 41 by means of the half mirror 44. The light transmitted by the half mirror 44 passes through the absorbance measuring chamber 25 into which the mixture was introduced. In this way, part of this light is absorbed by the absorbance component in the mixture, while the remainder of the component light is supplied to the transmitted light receiving unit 15 via the transmitted light guidance path 34. On the other hand, the light reflected by this half mirror 44 is supplied to the reflected light receiving part 46 via the reflected light guidance path 35.

The transmitted light receiving unit 15 outputs electrical signals for which integrated values of the peak intensity with respect to the received light have been photoelectrically converted as transmitted light signals (light intensity signals). The reflected light receiving part 46 outputs electrical signals for which integrated values of the peak intensity with respect to the received light have been photoelectrically converted as reflected light signals (light intensity signals). These transmitted light signals which have been output by the transmitted light receiving unit 15 and the reflected light signals which have been output by the reflected light receiving part 46 are input into the operation part 16, and based on these signals, the concentration of the portion of the substance to be determined is computed and displayed in the display part 19.

A light guidance path for selectively delivering the light which travels from the light source 13 in a straight line to the absorbance measuring chamber 25 is formed by the above described first absorbance testing device 10 by the aperture 41 in the absorbance measuring chamber 25. Therefore light with high parallelism can be allowed to be incident in the absorbance measuring chamber 25. Moreover, by the arrangement of the means for measuring the incident light intensity with the half mirror 44 and the reflected light receiving part 46, the incident light intensity and the transmitted light intensity can be measured at the same time. Furthermore, the half mirror 44 is arranged such that it crosses the aperture 41. The light passing through this aperture 41 is used to measure the incident light intensity. Therefore, even for a change of the amount of radiation of the light emitted by the light source 13 which occurs over time, it is prevented that only one of the measured values of the incident light intensity and of the transmitted light intensity which are used for computing the concentration of the portion of the substance which is to be determined fluctuates. Also, an exact value of the incident light intensity of the light which is introduced into the absorbance measuring chamber 25 can be obtained, even if the amount of light which passes through the aperture 41 does not change proportionally to the ratio of the change in the amount of radiant light of the light emitted from the light source 13 which occurs over time. Therefore, the concentration of the portion of the substance to be determined in the test liquid can be measured with high accuracy.

Here, it is imagined that the reason why the amount of light which passes through the aperture 41 does not change proportionally to the ratio of the change in the amount of radiation of the light emitted from the light source 13 which occurs over time is that, of the light which is emitted by the light source 13 through the aperture 41 with an extremely small opening diameter of, for example, 0.3 mm, only a tiny portion of the light which travels in a straight line to the absorbance measuring chamber 25 is selected.

The first microchip testing device 10 has a microchip and a chip holder. However, since there is a means for measuring the incident light intensity with the half mirror 44 and the reflected light receiving part 46 and since the measurement of the incident light intensity and the measurement of the transmitted light intensity can be performed at the same time, there is no danger that the value of the incident light intensity measured beforehand will differ from the actual incident light intensity at the instant of measurement of the transmitted light intensity because, when the microchip for measurement of the incident light intensity is replaced by the microchip for measurement of the transmitted light intensity, a subtle deviation occurs in the optical system. This deviation arises in the test device which, as suggested by the inventors in a co-pending application filed in the U.S. on Sep. 14, 2005 claiming priority of Japanese patent application 2004-274788 (U.S. application Ser. No. 11/225,044, filed Sep. 14, 2005), has a chip holder in which an optical path for introducing the light emitted by the microchip and the light source into the absorbance measuring chamber is formed, and in which a discharge lamp such as a xenon lamp or the like is used as the light source for supply of the light to the chamber for measuring absorbance. As a result of the formation of a subtle deviation in the course of the effort of inserting the microchip 20 into the chip holder 30 in the optical system of the device 10 itself, it is prevented that only one of the measured values of the incident light intensity and of the transmitted light intensity which are used for computing the concentration of the portion of the substance which is to be determined fluctuates. Consequently, the concentration of the portion of the substance to be determined in the test liquid can be measured with high precision.

Since, in the first microchip testing device 10, the absorbance measuring chamber 25 is located in the projection 22 in an offset state and projects beyond the other areas of the microchip 20, the degree of freedom of construction of the measurement system of the device 10 is great, by which the measurement error can be reduced.

The first microchip testing device of the invention can be changed in different ways, such as, for example, instead of the half mirror, a mirror with the property (hereinafter also called the "wavelength selection mirror") that only light of a certain wavelength range (specifically light in the measurement wavelength range) is transmitted and light in a wavelength range outside of a certain wavelength range (hereinafter also called only "light in a different wavelength range") is reflected can be used.

Figure 5:
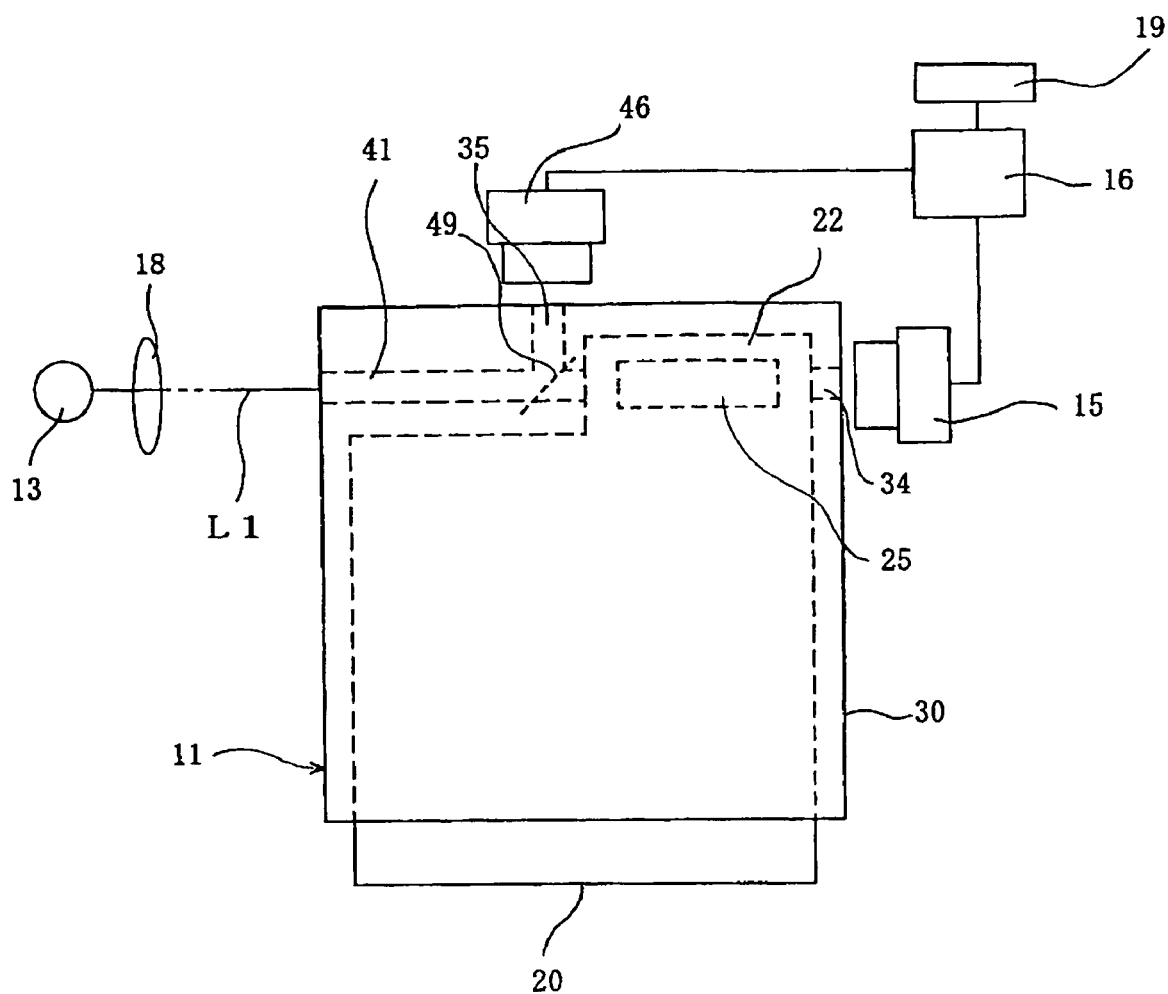
FIG. 5 is a schematic representation of another embodiment of the arrangement of the microchip testing device in accordance with the invention.

In such a microchip testing device, as shown in FIG. 5, the light in the measurement wavelength range which has been transmitted by a wavelength selection mirror 49 is supplied to the transmitted light receiving unit 15. Light in the other wavelength range is supplied to the reflected light receiving part 46. Using the proportional relation between the amount of light in this measurement wavelength range and the amount of light in the other wavelength range, the concentration of the substance to be determined in the liquid to be tested is measured.

In this case, light in the measurement wavelength range can be selected by the wavelength selection filter 49 from the light emitted by the light source 13. Therefore, it is unnecessary to arrange a wavelength selection filter. Furthermore, compared to the microchip testing device using a half mirror which divides the light in the measurement wavelength range from the light emitted by the light source for measuring the transmitted light intensity and for measuring the incident light intensity into two component light paths, since the intensity of the light which is supplied to the transmitted light receiving unit 15 and the reflected light receiving part 46 is greater, even higher measurement accuracy can be obtained.

SECOND EMBODIMENT

Figure 6:
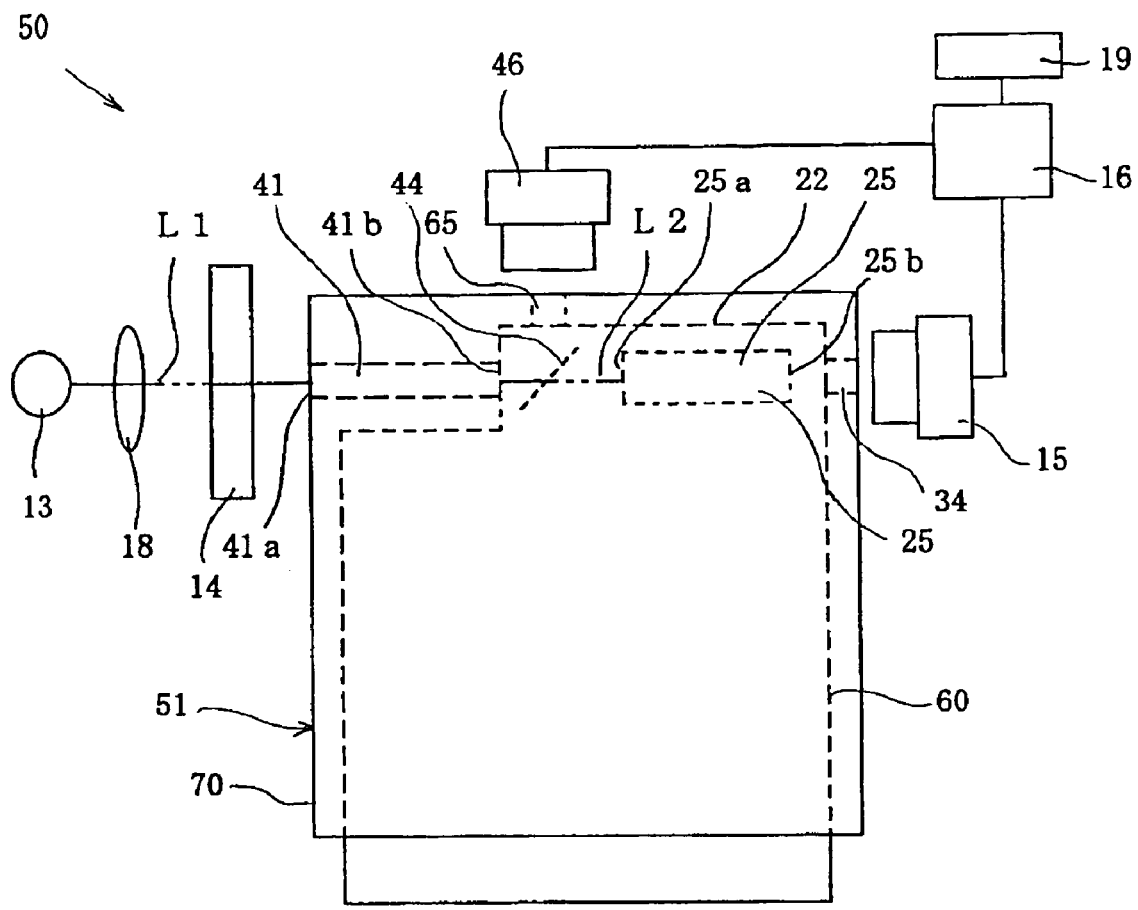
FIG. 6 is a schematic representation of still another example of an arrangement of the microchip testing device in accordance with the invention.

FIG. 6 is a schematic of another example of the arrangement of the microchip testing device as claimed in the invention. This second microchip testing device 50, besides the arrangement of a half mirror 44 in the microchip 60, has the same arrangement as the first microchip testing device 10 according to the first embodiment.

In FIG. 6, the components with the same arrangements as the components of the first microchip testing device 10 are provided with the same reference numbers. Here, a reflected light guidance path 65 delivers the light reflected by the half mirror 44 to the reflected light receiving part 46.

In the microchip 60, comprising the main body 51 of the device of the second microchip testing device 50, the half mirror 44 is located upstream from the light incident surface 25a of the absorbance measuring chamber 25 in the projection 22 (on the left in FIG. 5). This half mirror 44 is arranged inclined at an angle of 45° with respect to the optical path L2 (shown in FIG. 6) in which the light which has emerged from the light exit end 41b of the aperture 41 which is located in the chip holder 70 travels to the absorbance measuring chamber 25.

Here, the microchip 60, besides the arrangement of the half mirror 44 in the projection 22, has the same arrangement as the microchip 20 in the first microchip testing device 10.

This microchip 60 is produced by cementing two substrates. It can be produced of the following components as follows:

Components:
  an opening for injection of the liquid to be tested;
  a through opening for forming an opening for injection of reagent and for formation of an outlet opening;
  an absorbance measuring chamber;
  a mixing chamber;
  recessed areas for forming extremely small channels which connect the openings, the mixing chamber and the absorbance measuring chamber continuously to one another (specifically a channel for the liquid to be tested which continuously connects the opening for injection of the liquid to be tested to the mixing chamber, a reagent channel which continuously connects the opening for injection of reagent to the mixing chamber, a channel for mixing which continuously connects the mixing chamber to the absorbance measuring chamber, and an outlet channel which continuously connects the absorbance measuring chamber to the outlet opening);
  a substrate which is provided with a recess for installation of the half mirror (hereinafter also called "first substrate");
  another substrate (hereinafter also called "second substrate"); and
  a half mirror 44 installed in the half mirror installation recess of the first substrate.
  After installation of the mirror in the first substrate, the substrates are cemented together such that the recesses provided in the first substrate are hermetically sealed.

In the second microchip testing device 50 with this arrangement, the light in the measurement wavelength range which is emitted by the light source 13 and which has been transmitted by the wavelength selection filter 14, after passing through the aperture 41 is divided by means of the half mirror 44 into two light components. Moreover, the light reflected by the half mirror 44 is supplied via the reflected light guidance path 65 to the reflected light receiving part 46. Besides this circumstance, however, in the operation part 16 the concentration of the portion of the substance to be determined is computed and displayed in display part 19 in the same way as in the first microchip testing device 10 based on the transmitted light signals which have been output by the transmitted light receiving unit 15 and based on the reflected light signals which have been output by the reflected light receiving part 46.

The aperture 41 forms a light guidance path for selective introduction of light into the absorbance measuring chamber 25, which light travels from the light source 13 to this absorbance measuring chamber 25 by the above described second microchip testing device 50. Therefore, light with high parallelism can be allowed to be incident in the absorbance measuring chamber 25. Moreover, since there is a means for measuring the incident light intensity from the half mirror 44 which is located in the optical path L2 in which the light emerging from the other end 41b of the aperture 41 travels to the absorbance measuring chamber 25, and from the reflected light receiving part 46, the incident light intensity can be measured using the light which has passed through the aperture 41 together with the measurement of the transmitted light intensity. Therefore, even for a change in the amount of radiation of the light emitted by the light source 13 which occurs over time, it is prevented that only one of the measured values of the incident light intensity and of the transmitted light intensity which are used for computing the concentration of the portion of the substance which is to be determined fluctuates. Also, an exact value of the incident light intensity of the light which is introduced into the absorbance measuring chamber 25 can be obtained, even if the amount of the light which passes through the aperture 41 does not change proportionally to the ratio of the change of the amount of radiant light of the light emitted from the light source 13 which occurs over time. Therefore, the concentration of the portion of the substance to be determined in the test liquid can be measured with high accuracy.

The second microchip testing device 50 has a microchip 60 and a chip holder 70. Since measurement of the incident light intensity and measurement of the transmitted light intensity can be performed at the same time, it can be prevented that only one of the measured values of the incident light intensity and of the transmitted light intensity which are used for computing the concentration of the portion of the substance which is to be determined fluctuates even if in the course of the effort of installing the microchip 60 in the chip holder 70 a subtle deviation occurs in the optical system of the device 50 itself. Therefore, the concentration of the portion of the substance to be determined in the test liquid can be measured with high accuracy.

The second microchip testing device of the invention can be changed in different ways, such as, for example, instead of the half mirror, using a wavelength selection mirror, as in the first microchip testing device.

The microchip testing device in accordance with the invention was described above using two specific embodiments. The invention is however not limited thereto, but for the microchip testing device according to the invention suitable parts can be used for other material components if the microchip testing device has a microchip with a chamber for measuring absorbance, the light which has been transmitted through this chamber and emitted by the light source is received by the transmitted light receiving unit and if there are an aperture, a beam splitter of incident light which is either a half mirror or a wavelength selection mirror, and a reflected light receiving part.

For example, the concentration of γ-GTP in the blood, the concentration of GOT and the like can be measured by the above described microchip testing device in accordance with the invention.

The concentration of γ-GTP in the blood can be measured as follows.

L-γ-glutamyl-3-carboxy-4-nitroanilide (GluCANA) and glycylglycine are used as the reagents.

As shown below using the reaction equation (1), the property is used that, by a reaction of γ-GTP with two different reagents, L-γ-glutamyl-glycylglycine and 5-amino-2-nitrobenzoic acid with the property of absorption of light of a wavelength of 405 nm are produced.

Thus the measurement is taken based on the amount of absorbance of the light with a wavelength of 405 nm by 5-amino-2-nitrobenzoic acid.

Reaction equation (1)

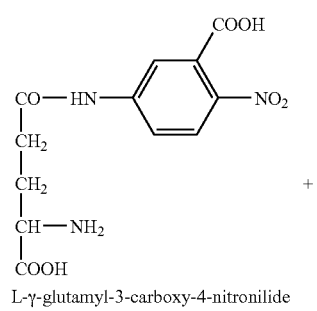

L-γ-glutamyl-3-carboxy-4-nitronilide

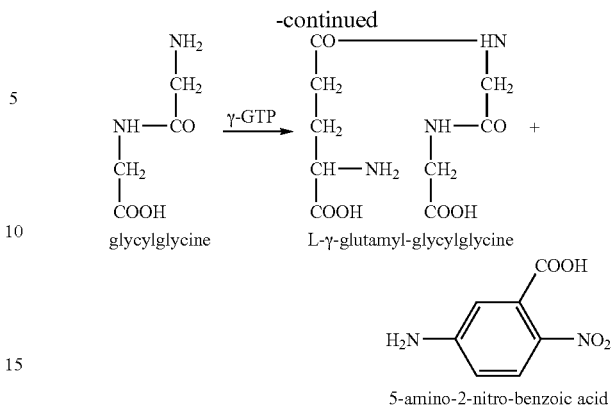

Furthermore, the concentration of GOT in the blood can be measured as follows:

The reagent used is β-nicotinamide-adenine-dinucleotide of the reduction type (NADH) solution with the property of absorption of light with a wavelength of 340 nm.

The property is used that by the reaction of GOT with the reagent, β-nicotinamide-adenine-dinucleotide of the oxidation type (NAD) is produced.

Thus, the measurement is taken based on the amount of absorption of light with a wavelength of 340 nm by β-nicotinamide-adenine-dinucleotide of the reduction type (NADH).

Specifically, a microchip testing device for taking the measurement of the concentration of γ-GTP in the blood with the specification described below is produced.

This microchip testing device has the arrangement shown in FIG. 1. A microchip of polyethylene terephthalate is used with a length of 25 mm, a width of 25 mm, a thickness of 2 mm, a height of the projection of 2.5 mm and a total length of the projection of 12 mm, in the absorbance measuring chamber the diameter of the light incidence surface and the light exit surface being 0.7 mm and its total length being 10 mm. A chip holder of aluminum was used with an aperture with an opening diameter of 0.3 mm, a total length of 16 mm and a ratio (a/b) of the opening diameter to the total length of 0.019.

The light source used was a xenon lamp of the short arc type. The wavelength selection filter was a filter with a high transmission factor only for light in the wavelength range of 400 nm to 410 nm (405±5 nm). A respective silicon photodiode was used as the transmitted light receiving unit and the reflected light receiving part.

With this microchip testing device several concentration measurements were taken using 1 μl to 2 μl blood as the liquid to be tested and using 2.1 μl of L-γ-glutamyl-3-carboxy-4-nitroanilide (GluCANA) and 8.4 μl glycylglycine as the reagents. In each of these repeated concentration measurements, the microchip was replaced. Between the time at which the first concentration measurement was taken and the time of the last concentration measurement, there was a major time difference, the amount of radiant light of the xenon lamp as the light source having been changed. However, the same measurement value was obtained for all lamps.

With this result, it was confirmed that high measurement accuracy can be obtained by the microchip testing device of the invention, even in the case of using a discharge lamp as the light source or in the case of formation of a subtle deviation in the optical system of the testing device itself.

What is claimed is:

1. Microchip testing device with
a microchip with an absorbance measuring chamber,
a transmitted light receiving unit for receiving light which has been emitted from a light source and has been transmitted through the absorbance measuring chamber,
an aperture, which extends in a straight line in a direction of an optical axis of the absorbance measuring chamber, having an inlet opening for the light emitted by the light source on one end and a light exit opening on an opposite end, by which the light enters the absorbance measuring chamber;
an incident light beam splitter located in the optical path between the light exit opening of the aperture and the absorbance measuring chamber and which transmits one part of the incident light and reflects another part of it, and
a reflected light receiving part for receiving the part of the incident light reflected by the beam splitter
wherein the microchip has a projection which protrudes beyond a partial section of one of its side edges and which has a side face which is opposite the light exit opening of the aperture and wherein the projection contains the chamber for measuring absorbance.

2. Microchip testing device with
a microchip with an absorbance measuring chamber,
a transmitted light receiving unit for receiving light which has been emitted from a light source and has been transmitted through the absorbance measuring chamber,
an aperture, which extends in a straight line in a direction of an optical axis of the absorbance measuring chamber, having an inlet opening for the light emitted by the light source on one end and a light exit opening on an opposite end, by which the light enters the absorbance measuring chamber;
an incident light beam splitter located in the optical path between the light exit opening of the aperture and the absorbance measuring chamber and which transmits one part of the incident light and reflects another part of it, and
a reflected light receiving part for receiving the part of the incident light reflected by the beam splitter
wherein the aperture is located in the microchip and the beam splitter is located in the optical path in an area between an entry surface for the light emitted by the light source into the microchip and the absorbance measuring chamber.

3. Microchip for use in a microchip testing device, comprising:
an absorbance measuring chamber though which light emitted by a light source is transmitted;
an elongated aperture, which extends in a straight line in a direction of an optical axis of the absorbance measuring chamber, having an inlet opening for the light emitted by the light source on one end and a light exit opening on an opposite end, by which the light enters the absorbance measuring chamber; and
an incident light beam splitter located in the optical path between the light exit opening of the aperture and the absorbance measuring chamber and which transmits part of the incident light and reflects another part of it, and
wherein the location of said beam splitter in the optical path is also in an area between an entry surface for light emitted by the light source into the microchip and the absorbance measuring chamber.

4. Microchip for use in a microchip testing device as claimed in claim 3, wherein the beam splitter is located in the optical path between the inlet opening and the light exit opening of the aperture.

* * * * *